United States Patent [19]
Pandian et al.

[11] Patent Number: 5,627,030
[45] Date of Patent: May 6, 1997

[54] METHOD OF AMPLIFICATION FOR INCREASING THE SENSITIVITY OF DETECTING NUCLEIC ACID-PROBE TARGET HYBRIDS

[75] Inventors: Sithian Pandian, Orleans; Eng J. Aw, Kanata; David I. Smith, Richmond, all of Canada

[73] Assignee: Kalyx Biosciences Inc., Canada

[21] Appl. No.: 275,849

[22] Filed: Jul. 15, 1994

[30] Foreign Application Priority Data

Jun. 28, 1994 [CA] Canada .................................... 2126952

[51] Int. Cl.$^6$ .............................. C07H 21/04; C12Q 1/68
[52] U.S. Cl. ................... 435/6; 435/5; 536/24.3; 935/77; 935/88
[58] Field of Search ............... 435/6, 5; 935/77, 935/78; 536/24.3

[56] References Cited

U.S. PATENT DOCUMENTS

| | | | |
|---|---|---|---|
| 5,124,246 | 6/1992 | Urdea et al. | 435/6 |
| 5,175,270 | 12/1992 | Nilsen et al. | 536/24.3 |
| 5,200,313 | 4/1993 | Carrico | 435/6 |

OTHER PUBLICATIONS

Matthews, J. et al. Aml. Biochem. 169: 1-25, 1988.

*Primary Examiner*—W. Gary Jones
*Assistant Examiner*—Paul B. Tran
*Attorney, Agent, or Firm*—Banner & Witcoff, Ltd.

[57] ABSTRACT

The present invention provides a method for simplifying and significantly enhancing the sensitivity of nucleic acid hybridization assays. A method is described whereby a single-stranded primary nucleic acid sequence that includes a region of sequences complementary to a single-stranded target nucleic acid sequence is hybridized to the target molecule. Stability of the double-stranded complex thereby formed can be enhanced by using RNA as the probe if DNA is the target or DNA as the probe if RNA is the target. The probe-target complex is subsequently immunocaptured for detection. After washing away extraneous material, a secondary nucleic acid sequence containing many repeating sequence units is hybridized to the probe component of the immobilized probe-target complex. Detection occurs following hybridization of many labelled nucleic acid sequence probes to each of the repeating sequence units of a nucleic acid amplification probe. Thus, attachment of multiple labelling probes to an amplification probe that is hybridized to an immobilized probe-target complex, provides a simplified method for amplifying the detection signal and therefore the sensitivity of nucleic acid hybridization assays.

20 Claims, 3 Drawing Sheets

I

II

III

IV

V 5,627,030

METHOD OF AMPLIFICATION FOR INCREASING THE SENSITIVITY OF DETECTING NUCLEIC ACID-PROBE TARGET HYBRIDS

BACKGROUND OF THE INVENTION

The present invention relates to nucleic acid hybridization assays which are useful as a means of locating specific nucleic acid sequences. Examples of nucleic acid sequences are deoxyribonucleic acid (DNA) and ribonucleic acid (RNA) sequences. The molecular subunits of both DNA and RNA are called nucleotides which are linked together to form long polynucleotide chains. Each nucleotide subunit is made of a sugar moiety, a phosphate moiety and a base moiety. It is the sequential ordering of the base moieties [adenine (A), cytosine (C), guanine (G), thymine (T), uracil (U)] that contains DNA or RNA's genetic information. The ordering of these base moieties in a polynucleotide chain and the tendency of the bases to attract and bond with other specific base moieties, is exploited by this invention to locate, detect and isolate specific DNA or RNA sequences.

DNA normally contains two polynucleotide strands twisted about one another lengthwise in a helical manner resembling a ladder where the sides are made of identical sugar (deoxyribose) and phosphate molecules while the rungs are made up of bases extending out from each strand, held together by weak attractive forces. In DNA, the base thymine on one strand always pairs with the base adenine on the opposing strand, and the base guanine always pairs with the base cytosine. This is called complementary base pairing.

RNA is also a polynucleotide strand. However, the sugar moiety is ribose (versus deoxyribose in DNA) and the bases are adenine, guanine, cytosine and uracil. In RNA, the base uracil on one strand always pairs with the base adenine on the opposing strand, and the base guanine always pairs with the base cytosine. Although RNA can pair with either a complementary strand of RNA or DNA, it is normally single stranded so does not form a helical structure.

The present invention is founded, in part, upon the technique that single stranded nucleic acid sequences can be combined, or hybridized, under appropriate conditions with complementary single stranded nucleic acid sequences to form double stranded molecules. This technique was developed as a means for detecting and/or and isolating particular nucleic acid sequences of interest. It has increased in popularity during recent years in its application for detecting the presence of the DNA or RNA within such pathogens as viruses, bacteria, or other microorganisms and therefore the presence of these pathogens themselves. The technique can also be used for other purposes such as to screen bacteria for antibiotic resistance, to aid in the diagnosis of genetic disorders (for example in sickle cell anaemia and thalassaemia), and to detect cancerous cells. Several applications have been developed for the microbiological analysis of clinical, food, environmental, and forensic samples. A general review of the technique and its present and future significance is provided in Biotechnology (August 1983), pp. 471–478 which is incorporated herein by reference.

The following definitions are provided to facilitate an understanding of the present invention. The term 'probe' refers to a nucleic acid sequence of which there are at least three types: the primary probe, the amplification probe, and the labelling probe. The primary probe contains at least one nucleic acid sequence that is complementary (or will base pair) to some portion of a nucleic acid sequence on the target DNA or RNA molecule of interest. The amplification probe contains sequences that are complimentary to some sequences on the primary probe, and contains a region that is typically of at least one type of repeating sequence unit. The labelling probe contains sequences complementary to one of the repeating sequence units, in addition to a chemical label. Labels are detectable chemical groups, either radioactive molecules or non-radioactive molecules and can include: radioactive isotopes; enzymatically active groups such as horse radish peroxidase; fluorescent agents; chemiluminescent agents; precipitating agents; and/or dyes. The term 'signal' is used loosely to indicate the detectable characteristic of a detectable chemical group, which can include: a change in the light adsorption characteristics of a reaction solution resulting from enzymatic action of an enzyme attached to a labelling probe acting on a substrate; the color or change in color of a dye; fluorescence; phosphorescence; radioactivity; or any other indicia that will be evident to one skilled in the art.

The amplification probe is so named because it is used to cause many detectable chemical labels to become attached to one probe-target complex, such that the resulting signal is amplified in direct proportion to the number of labelled probes that hybridize to the amplification probe. If the amplification probe were to contain only one sequence unit that comprises sequences compatible to the labelling probe, only one labelling probe would become attached to the probe-target complex, and the signal would not be amplified. However, the amplification probe disclosed in the present invention contains typically five or more sequence units that are compatible to the labelling probe, such that five labelling probes will attach to one probe-target complex, resulting in five times the amount of detectable chemical label signalling the presence of one probe-target complex; thus, the indication that one probe-target complex was formed will be amplified five times. Moreover, if the amplification probe contains twenty sequence units that are compatible to the labelling probe, twenty labelling probes will attach to one probe-target complex, resulting in twenty times the amount of detectable chemical label signalling the presence of one probe-target complex; the indication that one probe-target complex was formed will thereby be amplified twenty times. The degree of amplification is optional and can be manipulated by the design and construction of the amplification probe as described herein.

One objective of a nucleic acid hybridization assay is to detect the presence of a specific nucleic acid sequence (the target sequence) in a given sample by contacting the sample with a complementary nucleic acid sequence (the probe) under hybridising conditions and observing the formation or absence of any probe-target complexes. The probe-target complex can be detected directly by a label attached to the probe. The complex can also be detected indirectly through such techniques as the hybridization of another nucleic acid sequence conjugated to a label or by the binding of an antibody labelled with a detectable chemical group.

One detection strategy currently employed in the art is exemplified by PCT Application Ser. No. 84/03520 and EPA 124221 which use an enzyme labelled nucleic acid sequence to detect the probe-target complex by hybridization to complementary sequences on the tail of the probe. For example, the Enzo Biochem "Bio-Bridge" system uses a biotin molecule conjugated to a poly(A) tail (a nucleic acid sequence comprised solely of adenine nucleotides) as the detection system following hybridization of a DNA probe possessing a poly(T) tail (a nucleic acid sequence comprised solely of thymine nucleotides) to the target DNA sequence.

In order to employ such a technique as an assay, one must be able to detect the presence or absence of probe-target complexes with a high degree of sensitivity. The sensitivity of a nucleic acid hybridization assay is determined primarily by the detection limit of the label to demonstrate the formation of the probe-target complex against back-ground noise and/or false-positives. Different strategies have been employed to improve the sensitivity of nucleic acid hybridization assays, which can be classified into four broad categories: 1) separation of the probe-target complex; 2) target amplification; 3) probe amplification; 4) multiple labelling, or combinations thereof.

Some nucleic acid hybridization assays involve immobilization of the target sequence on a solid support followed by washing away the remainder of the reaction mixture. This first category involves techniques that attempt to either immobilize the target sequence before adding a label probe or use an immobilized labelled probe to capture the target nucleotide sequence. Alternatively, techniques have been developed that immobilize the probe-target complex after its formation. For example, EPA Publication No. 0225807 discloses a nucleic acid hybridization assay in which the probe-target complex is removed from solution by hybridization with a complementary solid-supported capture probe. The solid phase complex is then detected by subsequent hybridization to a labelled probe. Generally, procedures attempting to immobilize the probe-target complex at this stage using a nucleic acid sequence suffer from the fact that proteins and other materials in the heterogeneous sample may have a higher tendency to interfere with the immobilization of the nucleic acids. Furthermore, the sensitivity is low as the label to target ratio is 1:1.

A second category of strategies involves increasing the sensitivity of a nucleic acid hybridization assay through target amplification. An example of target amplification entails assaying for ribosomal RNA (rRNA) of a microorganism rather than chromosomal DNA. Since rRNA is present in any given cell at $10^4$ times higher concentration than DNA, the number of possible probe-target complexes increases, thereby increasing the probability of detecting the target organism. Alternatively, the polymerase chain reaction (PCR™) described in U.S. Pat. Nos. 4,683,105 and 4,683,202 has been used to amplify target nucleic acid sequences. The advantages and limitations of this technique has been reviewed by Gyllensten (Biotechniques 7, 700–706, 1989, incorporated herein by reference). For example, this transcription-based amplification system can produce a 2–5 million-fold amplification of a RNA target after 4 cycles (Lizardi et al., Biotechnology 6, 1197–1202, 1988). However, this technique suffers from such problems as excessive noise, false positives, requires considerable technical expertise, and relatively expensive instruments and reagents (Walcott et al. Food Protein 54: 387–401, 1991).

A third category of strategies for increasing the sensitivity of a nucleic acid hybridization assay entails probe amplification, by employing a combination of primary probes. Examples of this method are disclosed in U. S. Pat. Nos. 4,731,325 and 4,868,105 wherein techniques describe the use of more than one probe that binds to the target nucleic acid sequence. A further example is found in U.S. Pat. No. 4,868,105, where the labelled secondary probes hybridizes to the multiple primary probes bound to the target nucleic acid sequence.

Finally, some have attempted to employ multiple probes in a cascading or sandwich fashion as a strategy for amplifying the signal. These methods fall under the fourth category of signal amplification because they result in the attachment of multiple labelling groups to the primary probe-target complex. It is within this category that the present invention could be said to reside.

An early attempt to develop strategies within this fourth category is exemplified by PCT Application WO 90/13667 which describes an amplified solution-phase sandwich nucleic acid hybridization assay for the hepatitis B virus nucleic acid sequence in which the analyte is hybridized in solution with sets of amplifier probe polynucleotides and capture probe polynucleotides each have a first segment that is complementary to the target nucleic acid; furthermore, the amplifier probe has a second segment that is complementary to a unit of a polynucleotide multimer whereas the capture probe has a second segment that is complimentary to a polynucleotide bound to a solid phase. The resulting product is reacted with the polynucleotide bound to a solid phase and then with the multimer. The multimer probe is a chemically cross-linked single stranded oligodeoxyribonucleotide star-structured complex with arms possessing sequences complementary to the primary probe. Detection occurs when the bound materials are reacted with a labelled probe complementary to the polynucleotide units of the multimer.

In spite of the limited use of this strategy for detecting hepatitis B virus, the difficulties one would face devising the assay reagents are manifold, especially for general use. Constructing the chemical cross-linking in the secondary probe involves high levels of technical expertise as well as careful chemical modification of these polynucleotides in order to bring about the desired cross-linking. Overloading the star-like structures of the secondary probe can lead to steric hindrance between the star-like structures as well as between the anchoring arms attached to the solid phase. Furthermore, two sets of primary probes, both requiring the sequences complementary to the target nucleic acid, demand synthesis of probes designated to only one given target which is the case for a consensus hepatitis B virus double-stranded region sequence based on a multiplicity of hepatitis B viral subtypes. With these methods the cost of preparing probe reagents becomes significantly elevated eventually reflecting in the overall cost of the assay or the diagnostic kit. In short, this strategy is technically complex and the probe reagents are not applicable to a large variety of targets. Therefore, there remains a general need for a simpler system of signal amplification.

In yet a further method, Canadian Patent Application 2,039,517 provides a method for amplifying a signal wherein the amplification is obtained through use of a bridging nucleic acid sequence which can hybridize to the primary probe and to a developer nucleic acid sequence. This method entails hybridizing the primary probe to the target sequence, followed by exposure to the bridging sequence, followed by exposure to a first developer molecule, and finally followed by a second developer molecule to form a developer chain. One of the developer molecules is labelled, and the labelling can be detected in the developer chain. Again, the major limitation of this strategy is its complexity and there still remains a need for a simple system that allows for an increase in sensitivity.

A further method for this category is found in U.S. Pat. No. 4,716,106 where the primary probe sequence is first cloned in the filamentous phage M13 DNA. The single stranded form of the M13 DNA carrying the target-complementary sequence is isolated and then used as a primary probe. The DNA strand complementary to that carrying the probe is also separately isolated, labelled at multiple sites along its length and then used as the detector probe. Even though this assay involves the use of multiple labelling, this strategy necessarily involves cloning of the probe sequences in the M13 phage. Given the present molecular biology methodology, cloning of M13 is a difficult and cumbersome process, even for someone skilled in the art. The cloning must be performed every time anew in order to prepare the probe reagents directed towards a given target nucleic acid sequence. This increases the time, effort, and cost involved. Therefore, there remains a need for a simple and sensitive assay system for detection of specific nucleic acid sequences.

Due to the complexity and involvement of each of the strategies described above, these techniques are used to a limited extent by laboratories. Therefore, a need continues to exist for a simplified, rapid, and adaptable hybridization assay wherein a primary probe hybridizes to a target and to an amplifier polynucleotide strand that allows for attachment of multiple copies of a labelling molecule.

SUMMARY OF THE INVENTION

The present invention serves to overcome the limitations of the assays currently available in the art. Those ordinarily skilled in the art will appreciate that a preferred embodiment of the present invention provides a method for amplifying a signal during the detection of target nucleic acid sequences comprising:

a) hybridizing a polynucleotide probe (the primary probe) to the target nucleic acid sequence wherein the primary probe has a means for binding to a amplification nucleic acid sequence (the amplification probe), the amplifying molecule being capable of hybridizing to at least one labelling nucleic acid sequence, conjugated to a chemical label (the labelling probe);

b) immobilizing the probe-target complex;

c) exposing the immobilized probe-target complex to an amplification probe (a polynucleotide sequence containing a region of multiple repeating sequence units and a region of sequences complementary to sequences in a region of the primary probe) under conditions that allow the amplification probe to hybridize to the probe-target complex;

d) exposing the hybridized amplification probe to a labelling probe (a nucleic acid sequence conjugated to a chemical label and containing a region of sequences complementary to a repeating sequence unit on the amplification probe) under conditions that allow many labelling probes to hybridize to the amplification probe;

e) detecting the labelling probes in the resulting complex.

There are many advantages over the prior art attained by this invention. First and foremost, the present invention greatly facilitates label detection in nucleic acid hybridization assays by providing a plurality of repeating units in the amplification probe whereby it may receive up to 20 molecules (or more) of a selected labelling probe for every probe-target complex. This results in significantly increased sensitivity, and enhanced utility of hybridization assays.

A further advantage resides in the design of the probe used in the cascade of reactions. These probes could be easily and economically synthesized with the currently available methods and instruments. The rate of hybridization reaction is much higher in this invention due to the use of many shorter probes than when longer probes are used. Moreover, use of single stranded probes also avoids the problem of self-annealing of the probes during the hybridization reaction. Since the label is not directly linked to the primary probe, the hybridization properties of primary probe are not altered, which contributes to the ability of probe reagents to be applicable in a large number of target detection assays. Therefore, the preparation of such reagents is achieved by simple methods, reducing the overall cost of the assay.

Yet a further advantage is seen in the fact that since the primary probe could always be synthesized with a poly(A) sequence, the other components used in the assay such as the amplification probe and the labelling probe could be used universally in any nucleic acid hybridization assay. This translates into a large economy of efforts, costs, and uniformity of reaction conditions. Further, this allows the possibility for quickly developing assays for any given target; the only new requirement for each project would be the construction of the specific portion of the primary probe.

A further advantage of the present invention is to provide hybridization assays having less background noise, greater sensitivity, higher signal/noise ratios, as well as greater speed than has been achievable with previously known methods. Traditionally in nucleic acid hybridization assays, the primary probe is labelled with biotin or other markers along its entire length. When required to expedite the hybridization reaction using polynucleotides, such extensive modification of the probe might lead to a reduced efficiency of its hybridization with the target molecule and therefore the probe-target complexes might not be formed rapidly or stably. Since the primary probes of these traditional assays are end labelled, each of the probe-target complexes would carry only one marker and therefore the sensitivity of the assay would be limited to the detection of one marker per probe-target complex. In contrast, one embodiment of the present invention would amplify the signal by adding twenty or more marker molecules per each probe-target complex. The sensitivity of the assay would therefore be amplified to the extent proportional to the number of marker molecules attached to the amplification probe.

In a preferred embodiment of the present invention, a method is provided for amplifying a signal during the detection of target nucleic acid sequences in a test sample containing cellular material comprising the steps of hybridizing a polynucleotide probe (the primary probe) to the target nucleic acid sequence wherein the primary probe has a means for binding to a amplification nucleic acid sequence (the amplification probe), the amplifying molecule being capable of hybridizing to at least one labelling nucleic acid sequence, conjugated to a chemical label (the labelling probe); immobilizing the probe-target complex; exposing the immobilized probe-target complex to an amplification probe (a polynucleotide sequence containing a region of multiple repeating sequence units and a region of sequences complementary to sequences in a region of the primary probe) under conditions that allow the amplification probe to hybridize to the probe-target complex; exposing the hybridized amplification probe to a labelling probe (a nucleic acid sequence conjugated to a chemical label and containing a region of sequences complementary to a repeating sequence unit on the amplification probe) under conditions that allow many labelling probes to hybridize to the amplification probe; detecting the labelling probes in the resulting complex.

In a further preferred embodiment, this invention involves an amplification probe adapted to permit enhanced detectable labelling of a selected nucleic acid target, such probe comprising at least two regions of nucleic acid sequences: a first region including a sequence complementary to a sequence on a selected primary probe which also contains a sequence complementary to a sequence of said selected nucleic acid target, and a second region including a plurality of discretely labelable sequence units.

Yet another preferred embodiment of this invention involves a method for enhancing detectable labelling of probe-target complexes in nucleic acid hybridization assays incorporating an amplification probe adapted to permit enhanced detectable labelling of a selected nucleic acid target, such probe comprising at least two regions of nucleic acid sequences: a first region including a sequence complementary to a sequence on a selected primary probe which also contains a sequence complimentary to a sequence of said selected nucleic acid target, and a second region including a plurality of discretely labelable sequence units.

In a further preferred embodiment, this invention involves a method for detecting specific nucleic acid sequences comprising: a) hybridizing a first sequence of a primary polynucleotide probe to a selectable target nucleic acid sequence wherein the primary probe has a means for binding to an amplification probe comprising a nucleic acid sequence adapted to permit enhanced detectable labelling, the amplification probe being capable of hybridizing to at least one labelling probe comprising a nucleic acid sequence conjugated to a chemical label; b) immobilizing the target-probe complex; c) exposing the immobilized target-probe complex to said amplification probe, such probe comprising at least two regions of nucleic acid sequences: a first region including a sequence complementary to a sequence on a selected primary probe which also contains a sequence complementary to a sequence of said selected nucleic acid target, and a second region including a plurality of discretely labelable sequence units, under conditions that allows the amplification probe to hybridize to the target-probe complex; d) exposing the hybridized amplification probe to a labelling probe covalently attached to a detectable chemical label, such probe comprising sequences complementary to sequences on the amplification probe, under conditions that allows many labelling probes to hybridize to the amplification probe; e) observing the presence or absence of the detectable chemical label, covalently attached to said labelling probe, in association with the sample as indicating the presence or absence of the target sequence.

In yet another embodiment, this invention involves a reagent for detecting a particular polynucleotide sequence in a test sample, comprising: (i) a primary nucleic acid probe comprising at least one single stranded base sequence that is substantially complementary to the sequence to be detected; (ii) an antibody reagent capable of binding to hybrids formed between any of the particular polynucleotide sequences to be detected in the sample and the primary probe, but incapable of binding substantially to single stranded nucleic acids; (iii) an amplification probe adapted to permit enhanced detectable labelling of a selected nucleic acid target, such probe comprising at least two regions of nucleic acid sequences: a first region including a sequence complementary to a sequence of said selected nucleic acid target, and a second region including a plurality of discreetly labelable sequence units; (iv) a labelling probe covalently attached to a detectable chemical label, such probe comprising sequences complementary to sequences on the amplification probe.

Another embodiment of this invention involves a diagnostic kit for detecting a particular polynucleotide sequence within a sample comprising: (i) a primary nucleic acid probe comprising at least one single stranded base sequence that is substantially complementary to the sequence to be detected; (ii) an antibody reagent capable of binding to hybrids formed between any of the particular polynucleotide sequences to be detected in the sample and the primary probe, but incapable of binding substantially to single stranded nucleic acids; (iii) an amplification probe adapted to permit enhanced detectable labelling of a selected nucleic acid target, such probe comprising at least two regions of nucleic acid sequences: a first region including a sequence complementary to a sequence on a selected primary probe which also contains a sequence complementary to a sequence of said selected nucleic acid target, and a second region including a plurality of discretely labelable sequence units; (iv) a labelling probe covalently attached to a detectable chemical label, such probe comprising sequences complementary to sequences on the amplification probe.

In another embodiment, cells to be assayed are lysed with a lysis buffer solution and the nucleic acid sequences are denatured. The primary probe is contacted with the denatured nucleic acids in solution phase. Any probe-target complexes formed are removed from other material by immunocapture of the complexes. This is achieved by transferring the hybridization reaction mixture to microtiter plate wells that have been previously coated with monoclonal anti-probe-target complex. After washing, the immobilized probe-target complex is detected by contacting it with the amplification probe, then the labelling probe. The presence of an enzyme attached to the immobilized probe-target complex is determined by contacting the enzyme with its substrate and measuring the resulting reaction. Such an embodiment can involve the detection of *Listeria monocytogenes* in cheese, the detection of *Escherichia coli* in meat, or the detection of *Salmonella typhi* in human blood.

DESCRIPTION OF THE DRAWINGS

Certain embodiments of the invention may be seen from the Figures.

DETAILED DESCRIPTION OF THE INVENTION

Figure 1:
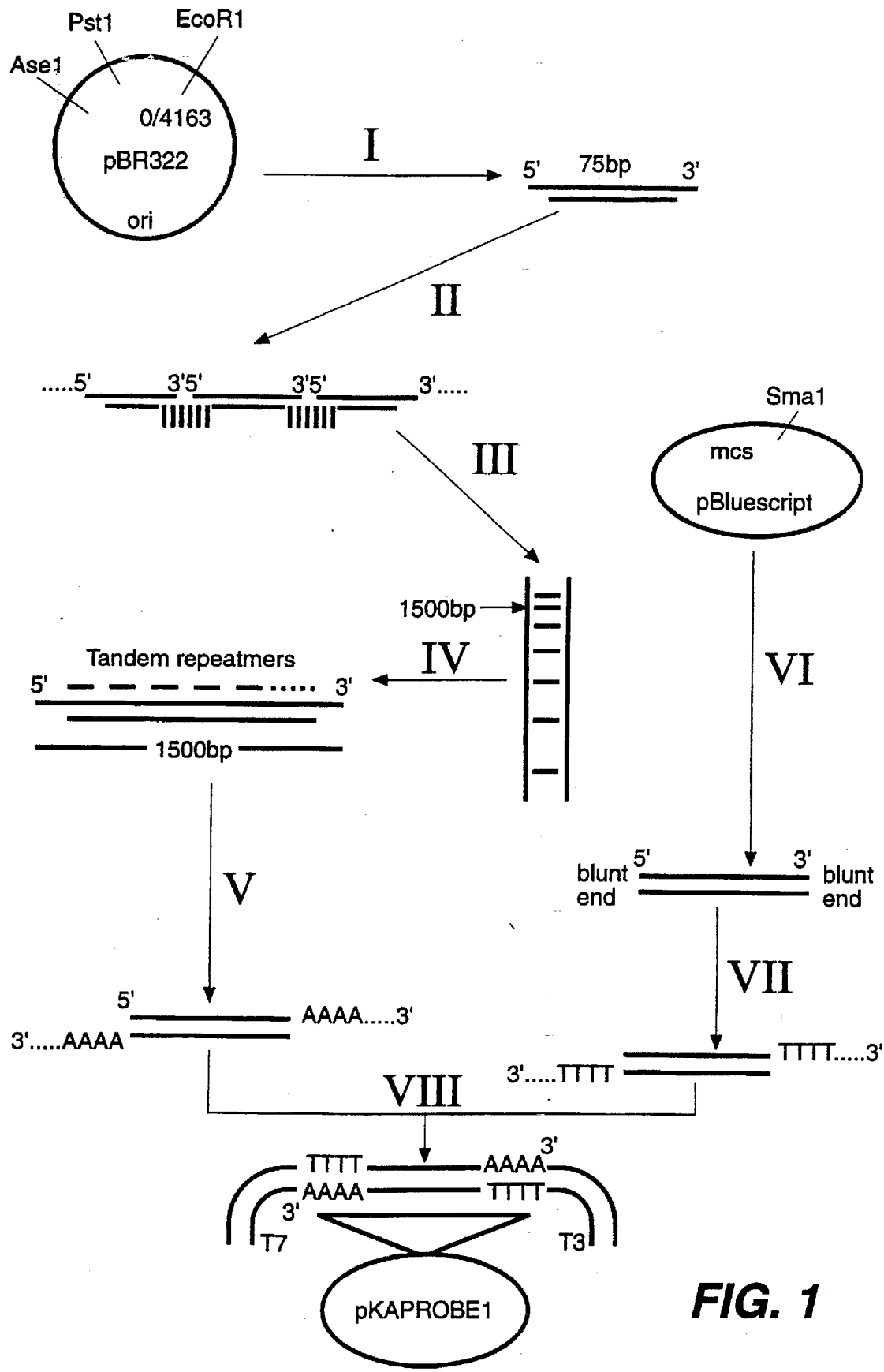
FIG. 1 is a schematic representation of plasmid preparation for reproducing the amplification probe. Step I entails i) digesting the plasmid pBR322 to completion with restriction enzyme Pst1, extracting the DNA and digesting to completion with the restriction enzyme Ase1; ii) electrophoresis of the digested segments of plasmid on polyacrylamide gel; and iii) isolation of the 75 bp fragment. Step II involves ligating the 75 bp fragment with the 5' TATGCA3' adaptor in the presence of T4 DNA ligase. The ligation reaction mixture is separated using electrophoresis. The 1500 bp fragment is extracted from the gel during Step IV. In Step V, the 1500-bp DNA fragment is treated with polynucleotidyl terminal transferase in the presence of dATP to add approximately 12–20 dAs to the 3' end of the DNA. Simultaneously, Step VI entails linearizing the plasmid pBluescript™ with restriction enzyme Sma1, and then treating it with polynucleotidyl terminal transferase in the presence of dTTP to add 12–20 dTs to the 3' end in Step VII. In the final step, Step VIII, the DNA sequences prepared in steps V and VII are mixed under appropriate conditions in order to anneal complementary tails and to form circular recombinant plasmid DNA.

This invention comprises the preparation of a number of nucleic acids sequence probes. This invention also comprises a method of simplifying and significantly amplifying the signal generated in a nucleic acid hybridization assay. The simplification and amplification is primarily achieved by using an amplification probe comprising multiple repeating sequence units and labelling probes that are complementary to the repeating sequence units.

The Target Nucleic Acid Sequence

The target nucleic acid sequences that can be detected in accordance with the present invention may be any nucleic acid sequence. There is no maximum limit to the length of the target nucleic acid sequence, though the minimum should be at least sixteen nucleotide bases in length.

The Primary Probe

The primary probe, which is single stranded nucleic acid sequence, has two distinct regions. At the 5' end, the sequence is complementary to a sequence found in the target, and such sequence is of sufficient length, ranging from at least 6 nucleotides up to a maximum of any length desired. In a preferred embodiment the length ranges from 16 to 25 nucleotides. The 3' end of this primary probe comprises a homopolymeric nucleotide tail [for example, a poly(dA)]. This poly(dA) sequence ranges in length, but must be sufficient to hybridize with the amplification probe. In a preferred embodiment the length ranges from 12 to 20 nucleotides.

When the target is DNA, the probe is preferably prepared in the form of RNA. When the target is RNA, the probe is preferably prepared in the form of DNA. When hybridization of the probe to the target results in an RNA-DNA hybrid, this is known as a heteroduplex. In a preferred embodiment, the homopolymeric region of the primary probe remains DNA in nature, though in the general embodiment, any type of nucleic acid sequence can be utilized in this region.

Techniques for synthesising a single-stranded polynucleotide sequence for the primary probe, which is complementary to the target sequence, are well known in the art and will not be described here.

The Antibody Reagent

Immobilization of the probe-target complex is achieved by using an antibody, attached to a surface, that binds to double-stranded nucleic acid. By separating the probe-target complex from the rest of the sample mixture, this procedure results in improved sensitivity of the detection of the target.

These particular antibodies are well known in the literature (Fliss et al., Appl. Environ. Microbiol. 59: 2608–2705, 1993; Coultee et al., Anal. Biochem. 181: 96–105, 1989; U.S. Pat. No. 5,200,313, all incorporated herein by reference) as is the procedure for the coating of the antibody molecules to a surface. Whole antibodies, antibody fragments, polyfunctional antibody aggregates, or in general any substance comprising one or more specific binding sites from an antibody for the probe-target complex can be utilized as described herein. Unless otherwise noted, it should be understood that, the term antibody when used in both the disclosure and the claims means whole antibodies and their polynucleotide and/or fragmented forms as well. When the term refers to a whole antibody, it may belong to any of the classes and subclasses of known immunoglogulins (IgG, IgM, etc.). It is also possible that a fragment of any such antibody which retains specific binding affinity for the hybridized probe can also be used, such as, the fragments of IgF which are often referred to as Fab, F(ab'), and F(ab)$_2$. Furthermore, aggregates, polymers, derivatives, and conjugates of immunoglobulins and/or their fragments can also be utilized where appropriate.

The antibody reagent's immunoglobulin source can be procured from any available techniques such as conventional antiserum and monoclonal techniques. Antiserum can be procured through well-known techniques involving the immunization of an animal, (such as mouse, rabbit, guinea pig or goat) with the appropriate immunogen. Furthermore, the immunoglobulins can be obtained by somatic cell hybridization techniques, which would result in the formation of monoclonal antibodies.

The preparation of immunogens for stimulating antibodies specific for heteropolymeric (ie. DNA-RNA or RNA-DNA) probe-target complexes can be achieved through a variety of techniques. For example, one can employ transcription of φX174 viron DNA with RNA polymerase (Nakazato, (1980) Biochem. 19: 2835, incorporated herein by reference). The resulting probe-target complexes can be adsorbed to a methylated protein, or they can be linked to a conventional immunologenic carrier material such as bovine serum albumin, before being injected into the desired host animal (Stollar, (1980) Meth. Enzymol. 70:70, incorporated herein by reference).

The most important property of any antibody raised against such target-probe double stranded complexes is that the antibody will significantly discriminate in its binding properties between the duplexed form of the target-probe complex and single stranded nucleic acid sequences. Achieving this objective is not difficult as the antibodies do not need to recognize specific sequences. Rather, they recognize the general double-stranded characteristic of the probe-target complex. This is a critical feature of this invention that significantly reduces background noise and false positives that could result from hybridization of labelling probe to non-target single stranded nucleic acid sequences in the sample.

It is preferred to use a solid support to which the antibody is attached or fixed. Attachment of the antibody can be achieved through either covalent or noncovalent bonds. The latter includes adsorption techniques that provide for a suitably stable and strong attachment. The solid support can take on a variety of shapes and compositions. These include beads, microparticles, porous and impermeable strips and membranes, as well as the interior surface of reaction vessels such as test tubes and microtiter plates, etc. The techniques for attaching a desired reaction partner to a selected solid support are well known to one skilled in the art.

The Amplification Probe

The amplification probe is the principal feature of this invention and serves to cause a plurality of delectable chemical labels to become attached to each amplification probe; in this way, the signal indicating the formation of one probe-target complex is amplified in direct proportion to the number of labelling probes that hybridize to the repeating sequence units.

The amplification probe is a single stranded nucleic acid sequence consisting of at least two regions. The first region contains a short nucleotide sequence complementary to a portion of the primary probe that permits the amplification probe to hybridize with the primary probe that is part of the immunocaptured probe-target complex. In one embodiment this first region is located on the 3' end and is comprised of a homopolymeric tail [e.g. poly(dA)] of approximately 12 to 20 nucleotides, but this can be extended up to any length desired.

The second region contains multiple repeating sequence units, that form the basis by which the detection indicia will be amplified when a labelling probe (containing sequences that are complementary to a region within one sequence unit) is hybridized to each of these repeating units. The number of repeating units can vary from 2 to as many as can be accommodated within a particular application of this invention. The greater the degree of amplification required for a given test system or the less sensitive the detection means to be employed, the larger the number of repeating units required. In one embodiment the number of repeating units is about 20.

The length of each unit can vary, dependant upon the requirements of a particular application of this invention. The minimum length of a repeating unit is about 16 nucleotides, though the best length is about 70–100 nucleotides. One critical factor to consider when designing the length of each repeating unit is the steric hinderance caused by the size of the detectable chemical label attached to the labelling probe. For example, a relatively large enzyme would require a greater degree of spacing than a small dye molecule or radioisotope. Moreover, the labelling probe should hybridize to only a portion of a repeating unit; the remaining nucleotides within the unit that are not complementary to the sequences of the labelling probe function as spacers to position the detectable chemical labels apart from one another. Furthermore, it will be understood that the subunits in the tandem repeating nucleic acid fragment orient in the same 5'→3' direction. In the example chosen in FIG. 1, each repeating sequence unit is 75 nucleotides long.

The repeating sequence units can be identical, or there can be more than different sequence unit. For example, it may be desirable to attach more than one type of detectable chemical label to the amplification probe, whereby a corresponding number of differently sequenced labelling probes will be required. In this situation one would construct the repeating sequence units with more than one type of sequence, each sequence being complementary to the sequence a type of labelling probe. For example, if it would be desirable for three types of labelling probes (eg. probe X, probe Y and probe Z) to attach to the amplification strand, the complementary repeating sequence units (unit x, unit y and unit z) on the amplification probe could be constructed in a xyzx-yzxyzxyz fashion. The nucleic acid sequences that are joined to form the repeating sequence region could each be constructed in a xyz fashion, such that when they are joined they will become linked in a xyz-xyz-xyz manner.

The construction of a plasmid that can be used to produce multiple copies of the amplification probe is prepared by well known techniques and one example is illustrated in FIG. 1. The DNA fragment coding for the amplification probe is cloned in an appropriate plasmid, such as pBluescript™, or any other suitable cloning vector. This plasmid is used as a template for the preparation of the amplification probe which consists of the complementary RNA copies of the repeating units and the homopolymeric nail.

The DNA Vector and Cloning

The experimental methods used to construct the DNA vectors used to reproduce the amplification probe are generally described in various manuals of molecular biology and are known to one who is skilled in the art (Sambrooke et al., Molecular cloning: A Laboratory Manual, 2nd edition. Cold Spring Harbor, N.Y., 1989, incorporated herein by reference).

In one instance, two hundred micrograms of the plasmid pBR322 (Bolivar et al., Gene 61: 253–264, 1977) were digested to completion with the restriction enzyme Pst1. The DNA was extracted with phenol-chloroform, ethanol precipitated and then digested to completion with the restriction enzyme Ase1. The digestion of pBR322 DNA with the restriction enzymes yielded a 75 nucleotide long fragment from the circular plasmid. This 75-base pair (bp) fragment was separated from the remainder of the plasmid by electrophoresis of the reaction mixture through an 8% polyacrylamide gel. The 75-bp fragment was isolated from the gel by the method of electro-elution using a Bio-Rad apparatus and the DNA was ethanol precipitated.

This 75-bp fragment was mixed with an adapter polynucleotide of the sequence 5'TATGCA3' in the presence of T-4 DNA ligase. This adapter-mediated ligation allowed polymerization of the 75-bp fragments with each of the subunits in the polymer being aligned in the same 5'→3' orientation. The ligation reaction mixture was electrophoresed through a 1% agarose gel and a ladder representing different polymeric sizes of the DNA was observed by ethidium bromide staining of the gel. From the gel, the DNA fragment corresponding to 1500-bp size was excised out and extracted from the gel using the QIAex gel extraction method (QIAGEN, Chartsworth, Calif.).

The above 1500-bp DNA was treated with polynucleotidyl terminal transferase in presence of dATP, to add approximately 12–20 dAs to the 3' end of the DNA. Simultaneously, the plasmid pBluescript™ (Stratagene, La Jolla Calif.) was linearized with the restriction enzyme Sma1 and then treated with the polynucleotidyl terminal transferase in presence of dTTP to add 12–20 dTs to the 3' end. The DNA sequences thereby prepared were mixed under appropriate conditions (GIBCO BRL Technical Bulletin 8008-1) in order to anneal complementary tails and to form circular recombinant plasmid DNA.

The annealed DNA was introduced into E. coli (Epicuriah E.coli XL-1; Stratagene, inc.) using a bacterial transformation procedure recommended by Stratgene. From the transformants, the colony containing the coding for the primary probe was confirmed by analysis of the plasmid DNA. The DNA of the plasmid coding for the primary probe was purified from the E. coli using the QIAgen megaPlasmid isolation kit.

Figure 2:
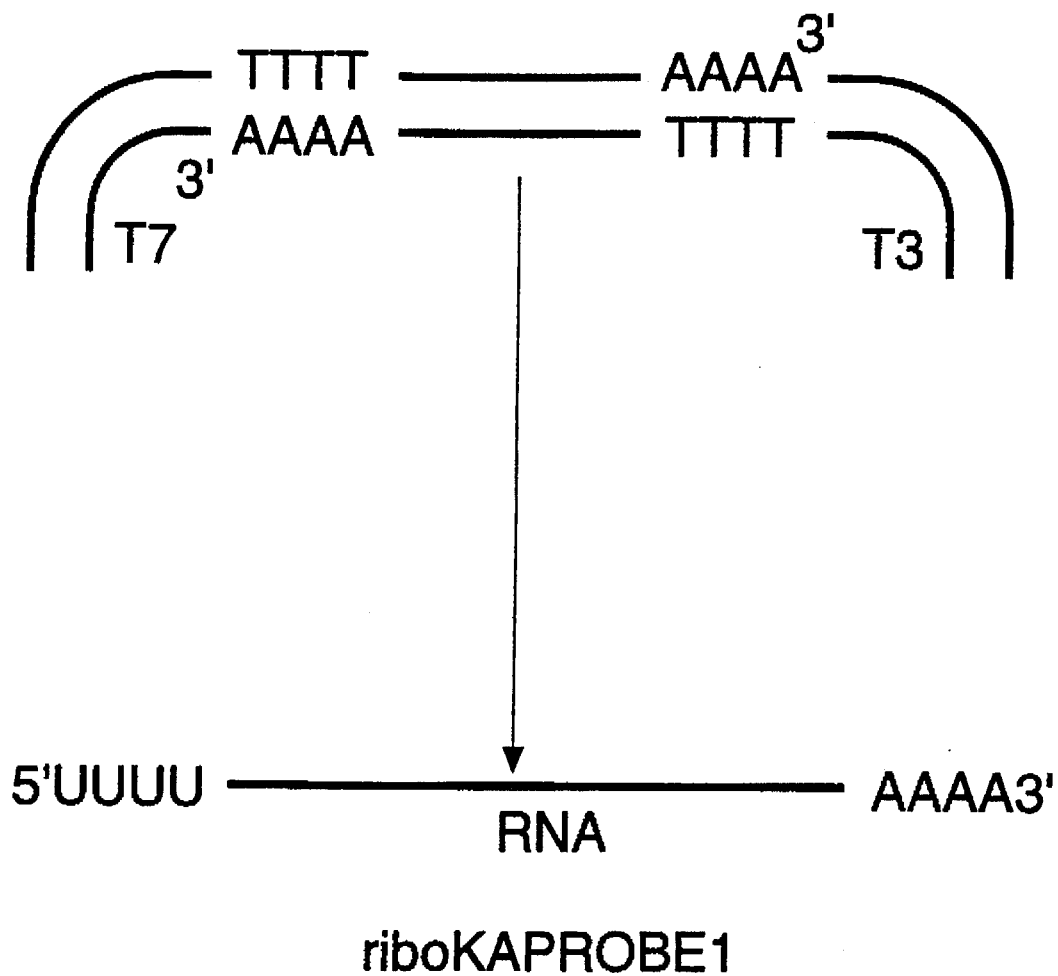
FIG. 2 is a schematic representation of the processes for preparing the amplification probe. In particular, it shows in vitro transcription with T7 polymerase.
Figure 3:
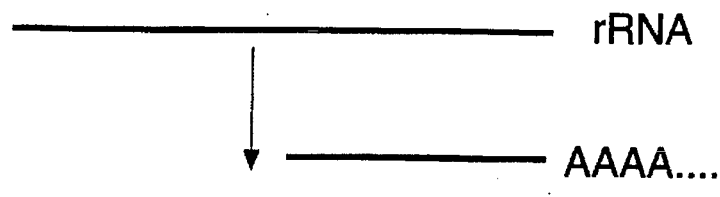
FIG. 3 depicts an embodiment wherein multiple probes are used in a sequential fashion in an assay for detecting a target nucleic acid sequence. In Step I, the cellular material is lysed, the nucleic acids are denatured and a specific synthetic DNA probe is added. Step II comprises hybridizing the specific DNA probe to the target nucleic acid within the sample to generate heteroduplex nucleic acid (HNA) complexes. The HNA complexes are immunocaptured by antibodies attached to a solid support such as a microtiter plate as depicted in Step III. Steps IV and V depict the series of steps involved in detecting the immunocaptured HNA complexes. In Step IV, riboKAPROBE is added and allowed to incubate for 30 minutes to enable hybridization with the 3' tail of the probe. Step V depicts: i) addition of KAR-25AP followed by a 30 minute incubation step; and ii) addition of substrate and subsequent incubation for 5 to 30 minutes. The developed color was then detected by conventional means.
Figure 3:
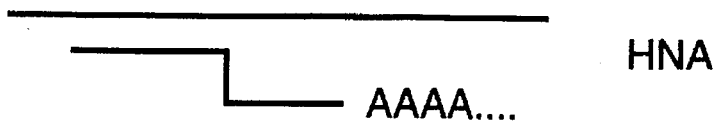
Figure 3:
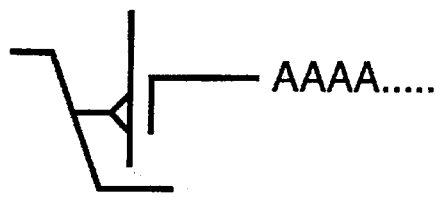
Figure 3:
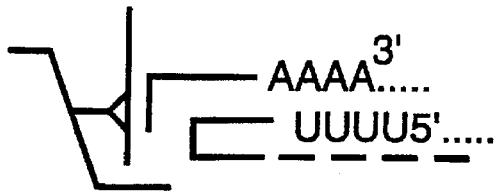
Figure 3:
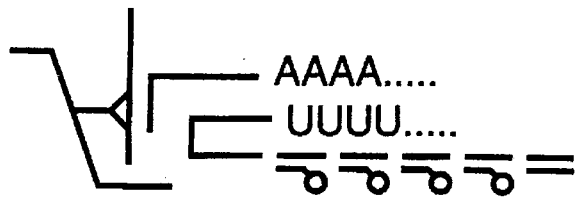

The procedure for transcribing DNA plasmid containing the nucleic acid sequence coding for the amplification probe is as follows. Plasmid DNA coding for the amplification probe (10 μg) was treated with the enzyme T-7 RNA polymerase in the method suggested by the MegaTranscription kit (Cat. No. 1334) supplied by Ambion Inc. (Austin, Tex.). This transcription generated an RNA product with a structure as shown in FIG. 2 comprising a poly (U) sequence at the 5' end.

An general, an in vitro transciption of the plasmid coding for the amplification probe using T-7 RNA polymerase would yield its complementary RNA, the amplification probe (FIG. 2) which carries a ploy (U) homopolymeric tail fragment at its 5' end; this ploy (U) region is complementary to the poly(A) region of the primary probe described previously. Recent advance in the are allows the large scale production of T-7 ploymerase mediated RNA molecules in an in vitro transcription. Kits such as "MEGA- Transcript kits" (Ambion Inc., Austin, Tex.) could be used to produce milligram quantities of RNA from microgram quantities of the template DNA.

It will be appreciated by one skilled in the art that once the amplification probe is constructed with an appropriate homopolymeric tail, the same template could be used for the production of an amplification probe which could be used in any nucleic acid hybridization assay wherein the primary probe comprises a sequence complementary to the homopolymeric region in the amplification probe.

The Labelling Probe

The immunocaptured probe-target complex can be detected by a variety of well known techniques. In a preferred embodiment, a labelling probe comprising sequences complimentary to at least one of the repeating sequence units on the amplification probe will itself be labelled with a chemical group that is detectable. A detectable chemical group can comprise any material possessing a detectable chemical or physical property. These materials are well known and developed in nucleic acid hybridization assays. Furthermore, most labels useful in such methods can be applied to the present invention. For example, enzymatically active groups have been found to be useful, in particular, those groups that are enzymes (Clin. Chem. (1976) 22: 1243; U.S. Pat. No. 2,019,408 and UK Pat. 31,006), enzyme substrates (U.S. Pat. No. 4,492,751), cofactors (see U.S. Pat. Nos. 4,230.797 and 4,238,565), and enzyme inhibitors (see U.S. Pat. No. 4,134,792). Also useful are fluorescers (see Clin. Chem. (1979)25: 353), chromophores, luminescers such as chemiluminescers and bioluminescers (U.S. Pat. No. 4,380,580), as well as specifically bindable ligands such as biotin (European Pat. Spec. 63,879) or a hapten (U.S. Pat. No. 4,380,580), and radioisotopes such as $^3H$, $^{14}C$, $^{32}P$, $^{35}S$, and $^{125}I$. These labels and labelling pairs are therefore detectable on the basis of either their own physical properties (eg., fluorescers, chromophores and radioisotopes), or their reactive, or binding properties (eg., enzymes, substrates, cofactors and inhibitors). A good example, is a cofactor- labelled antibody that can be detected by addition of the enzyme for which the label is both a cofactor and a substrate for that enzyme. More specifically a hapten or ligand labelled antibody can be detected by adding an antibody to the hapten or a protein (e.g., avidin) which binds the ligand, tagged with a molecule capable of detection. These detectable molecules can be a molecule possessing either a measurable physical property (e.g., fluorescence or absorbance) or a quality capable of participating in an enzyme reaction (see above for list). In one example, one can utilize an enzyme which acts upon a substrate to generate a product with a measurable physical property. Specific examples of this kind include, but are not limited to, β-galactosidase, alkaline peroxidase and phosphatase. Other similar labelling schemes are evident to one skill in the art.

The nature and the quantity of the label in the labelling probes are not critical. The probes could be labelled either at their extremities or along their entire length with a single or a multiple marker which, of course, can be any detectable substance; in other words, the probe is isotopically or chemically modified in such a way that the person performing the assay can, after further manipulation if necessary, still detect the presence of these labels.

The length of the hybridizing portion of the labelling probe can vary to meet the needs of application of the invention. The minimum length of the probe is about 16 nucleotides and the maximum length is about 25 nucleotides, though a situation may arise where it may be favourable to extend the length beyond 25 nucleotides. In a specific instance, a 25 base polynucleotide fragment with a 5' amino modification was commercially obtained (Bio/Can Scientific Co, Mississauga, Ontario). The sequence in this fragment was complementary to a region within the repeating unit sequence of the amplification probe. The amino modification allowed covalent coupling of the enzyme alkaline phosphatase to the 3' end of the sequence. The covalent attachment of the enzyme to the polynucleotide was carried out according to known methodology (Bio/Can Scientific Co.).

Variations on the design of the labelling probe and the amplification probe may be desirable. For example, the amplification probe itself can be labelled with biotin during the in vitro transcription, or end labelled separately. The labelling probe could be labelled with multiple markers rather than with just a single marker as shown in FIG. 1. As long as the labelling is performed in such a manner as to not interfere with the hybridization between the amplification and labelling probes, these supplementary labels can lead to a proportional increase in sensitivity of the assay.

This invention describes a general method of constructing the probe cascade. In a general embodiment, the cascade consists of a primary probe, an amplification probe, and a labelling probe with chemical and functional characteristics as described herewithin. The exact sequences implicated in the construction of the probe reagents described above (excepting, of course, the target complementary sequence in the primary probe) are not critical, and only the complementarity of the sequences to be hybridized is important. The exact lengths of the various probes described here are not limited to the sizes given in the examples herein. A person skilled in the art may easily vary these lengths and the methods for achieving such variation are well known in the art.

The Assay

The present invention is useful in a large variety of hybridization procedures. The sample to be assayed can be virtually of any medium of interest, such as of medical, veterinary, environmental, nutritional or industrial significance.

One embodiment of this invention comprises a sensitive method of detecting the probe-target complex and its application to the determination of the presence of specific microorganisms in a test sample. An assay, according to the present invention, involves at least the following steps:

a) hybridizing a sequence of a primary polynucleotide probe to a target nucleic acid sequence;

b) immobilizing the probe-target complex;

c) exposing the immobilized probe-target complex to an amplification probe under conditions that allows the amplification probe to hybridize to the probe-target complex;

d) exposing the hybridized amplification probe to many copies of a labelled polynucleotide probe under conditions that allows many such labelled probes to hybridize to the amplification probe;

e) detecting the labelled probes in the resulting complex.

In one particular embodiment, the sample to be tested is typically a piece of food, for example meat or cheese, or another source containing principally double stranded nucleic acids. This includes microorganisms and/or other cellular material associated with these samples. The test sample is first treated to release the nucleic acids from the cells, followed by a denaturation step to denature the nucleic acids. This is typically accomplished by lysing the cells in a lysis buffer solution and the denaturation of nucleic acids is preferably accomplished by heating the resulting solution in boiling water or alkali treatment (e.g., 0.1N sodium hydroxide). The denaturing step can often be used simultaneously as a method to lyse cells. The release of nucleic acids can, also, be obtained through mechanical disruption such as freezing/thawing, abrasion, sonication, physical/chemical disruption (eg. polyoxyethylene ether detergents like Triton®, polyoxytheylenesorbitan detergents like Tween®, sodium dodecylsulfate, alkali treatment, osmotic shock, heat, or lysing using enzymes such as proteinase K, lysozyme, pepsin). The resulting medium will contain nucleic acids in single stranded form which is then assayed according to present hybridization methods (Wang et al., Appl. Environ. Microbiol., 1992).

When the sample contains free single-stranded nucleic acid sequences, the sample is in proper form for use with the specific probe. When the assay is performed for detection of a microorganism, a bacterium for example, the cells must be lysed and the nucleic acids have to be exposed in order to be available for hybridization with the probe. Methods of lysis have been previously described and are well known to one skilled in the art.

in one general embodiment, the cells are lysed by mixing 50 µl of the broth culture (about $10^8$ to $10^9$ cells per ml) with an equal volume of a 2% Triton X-100® and heating at 100° C. for 5 minutes in a 1.5 ml eppendorf microfuge tube. The samples are chilled in ice to denature the target nucleic acids. The probe is diluted at a concentration of 200 ng per ml in a buffer containing 8×SSC (1×SSC being 0.15M NaCl plus 0.015M sodium citrate), 40 mM HEPES (pH 7.4) and 4 mM EDTA. One hundred µl of the probe thus prepared is added to the cell lysate so that the probe is contacted with the target nucleic acid and the hybridization is carried out in this solution at 70° C. for 30 minutes.

There are a variety of known hybridization conditions that can be employed in the assay. Typically, hybridization will proceed at slightly elevated temperatures. Typical temperatures range between about 35° and 75° C. and are usually about 65° C. The hybridization is carried out in a solution comprised of a buffer at pH between about 6 and 8 and with the appropriate ionic strength. A typical ionic strength is 2×SCC where 1×SCC=0.15M sodium chloride and 0.015M sodium citrate at pH 7. The hybridization solution further contains protein such as bovine serum albumin, Ficoll™ (copolymer of sucrose and epichlorohydrin, Pharmacia Fine Chemicals, Piscataway, N.Y.), polyvinylpyrrolidone, and a denatured foreign DNA such as rom calf thymus or salmon sperm. The degree of complementarity between the target nucleic acid sequence and the primary probe required for hybridization to occur depends on the stringency of the conditions.

The primary probe is contacted with the denatured nucleic acid sequences in solution phase. The probe-target complexes are removed from the excess unhybridized probe by immunocapture of the former. This is achieved by transferring the hybridization reaction mixture to the wells of a microtiter plate which have been previously coated with monoclonal anti-probe-target complex. The antibody is thus contacted with the probe-target complex present in the hybridization reaction mixture for 30 minutes at 37° C. This contact results in the immunocapture of the probe-target complexes and therefore results in their immobilization to the surface of the wells of the microtiter plate. Any reagent which will subsequently bind to the probe-target complex will thus be immobilized to the solid surface. After the immunocapture reaction is completed, the plates are washed three times with phosphate buffered saline (PBS; 50 mM phosphate buffer containing 0.15M NaCl) in order to remove the excess unhybridized probes from the well.

Alternatively, any other solid phase could be employed for the immunocapture of the probe-target complexes; any method of immobilisation of the probe-target complex could be used for separating the hybridized probe from the excess unhybridized probe.

In one embodiment, the amplification probe is diluted to a concentration of 200 ng per ml in a buffer containing 4×SSC, 20 mM HEPES (pH 7.4) and 2 mM EDTA. Two hundred µl of the amplification probe thus prepared are added to the wells of the microtiter plate so that the amplification probe is contacted with the immobilized probe-target complex which carries the poly(dA)$_{12-20}$ at the 3' end of the probe. The plates are incubated at 42° C. for 30 minutes so that the hybridization between the poly(dA) of the probe and the poly(U) of the amplification probe is completed. This poly(dA)-poly(U) is also a DNA-RNA hybrid, thermodynamically the most stable form of a double stranded nucleic acid. At the end of this hybridization period, the plates are washed three times with 0.5M sodium chloride solution.

The labelling probe is diluted to a concentration of 200 ng per ml containing 4×SSC, 20 mM HEPES (pH 7.4) and 2 mM EDTA. Two hundred µl of said labelling probe is added to the microtiter plate wells so that the labelling probes come in contact with the amplification probes which are immobilized to the solid surface. This hybridization is carried out at 42° C. for 30 minutes and the plates are then washed three times with 0.5M sodium chloride.

The labelling probe hybridizes with the repeating units of the amplification probe. As the labelling probe is a single stranded polynucleotide, the rate of the hybridization reaction is considerably high.

when the amplification probe comprises twenty repeating units, twenty labelling probe molecules can be immobilized per each of the probe-target complexes originally immunocaptured. The signal generated by the probe-target complex is amplified by a magnitude of twenty times. The enzyme present in the labelling probe is then detected using standard colorimetric, chemiluminescent, fluorometric or other detection methods as discussed herein and is well known in the art.

In one embodiment employing colorimetric methods, a solution containing the substrate to alkaline phosphatase enzyme is added to the wells. For example, 200 µl of p-nitrophenyl phosphate (p-NPP; 4 mg in 10% diethanolamine and 0.5 mM magnesium chloride, pH 9.8) are added. After 15 minutes of incubation at room temperature (20°–25° C.), the color developed is measured at 410 nm wavelength of light.

Reagent System

Another embodiment of the present invention involves its use in a diagnostic kit, the kit comprising one or more solutions and devices for carrying out an assay for detection of food pathogens such as *Listeria monocytogenes* or *Escherichia coli* 0157: H7 in food samples like cheese or meat.

The present invention further provides for a reagent system. More specifically it provides for a reagent combination comprising all of the essential and necessary elements required to conduct a desired assay method. The reagent system is presented in a commercially packaged form as a composition or a mixture wherein compatibility of the reagents will allow for a test device configuration (most typically as a test kit) a packaged combination of one or more containers, devices, or the like, holding the necessary reagents and usually including written instructions describing the performance of the assays. Reagent systems of the present invention involve all possible configurations and compositions for performing the various hybridization formats described herein.

The reagent system will generally comprise bacterial lysis solutions, the solutions containing the target directed primary probe, the amplification probe, the labelling probe (preferably labelled with a detectable chemical group) enzyme substrates, microtiter plates or strips coated with the anti-target-probe complex antibodies, and a description of the assay comprehensible to one skilled in the art. A test kit form of the reagent system may further include ancillary chemicals. Such ancillary chemicals can include components of the hybridization solution and denaturation agents capable of converting double stranded nucleic acids found in a test sample into single stranded form. More preferably, there is included a chemical lysing and denaturing agent, such as an alkali, for treating the sample in order to release single stranded nucleic acid therefrom.

The present invention will now be illustrated, but is not intended to be limited, by the following examples.

EXAMPLE 1

Assay for *Salmonella typhi* in human blood

A volume of 0.05 ml of blood was drawn from the test patient and was inoculated into 10 ml of Gram-negative broth (Difco) and incubated at 37° C. for 16–20 hours. Any bacteria in 100 µl of the enriched broth were lysed by mixing the broth with an equal volume of 2% Triton X-100 in a microfuge tube and boiling for 5 minutes at 100° C. The solution was quickly chilled in ice. Probe solution (100 µl; 200 ng per ml) in 8×SSC, 40 mM HEPES (pH 7.4) and 4 mM EDTA was added to the lysate and incubated at 37° C. for 30 minutes. The probe selected here was RNA in nature and specifically hybridising with the Vi antigen gene of *S. typhi*.

The above hybridization reaction mixture (200 µl) was transferred to microtiter plate well which had been previously coated with monoclonal anti-probe-target complex antibodies and incubated at 37° C. for 30 minutes. The plates were then washed 3 times with PBS.

Detection of any target nucleic acid entailed adding the amplification probe solution (200 µl; 200 ng/ul) in 4×SSC, 20 mM HEPES (pH 7.4) and 2 mM EDTA to the wells and incubating at 37° C. for 30 minutes. The plates were then washed 3 times with 0.5M sodium chloride solution. The labelling probe solution (200 µl; 200 ng/ul) in 4×SSC, 20 mM HEPES (pH 7.4) and 2 mM EDTA was added to the wells and incubated at 37° C. for 30 minutes. The plates were washed 3 times with 0.5M sodium chloride solution. Alkaline phosphatase substrate solution (4 mg of p-NPP in 10% diethanolamine and 0.5 mM magnesium chloride, pH 9.8) was added to the wells and incubated at room temperature for 15 to 30 minutes and the color developed was measured at 410 nm in a standard microtiter plate reader.

With the help of positive and negative controls, a colorimetric value was chosen that was statistically distinct between samples that contained, and those that do not contain *S. typhi*. Using this "cut-off value", the color generated was interpreted as to whether the original sample was positive or negative for the presence of the pathogen.

EXAMPLE 2

Assay for the detection of *L. Monocytogenes* in cheese

Twenty five grams of the test cheese was homogenized for 2 minutes in a stomacher with 250 ml of 1% sterile peptone water and allowed to settle for about 15 minutes. A 0.5 ml sample of the clear upper portion of this homogenate was inoculated into 10 ml of trypticase soy −0.6% yeast extract broth and incubated at 37° C. for 16–20 hours.

Any bacteria in 100 µl of the enriched broth was lysed by mixing the broth with an equal volume of 2% Triton X-100 in a microfuge tube and boiling for 5 minutes at 100° C. The solution was quickly chilled in ice.

Probe solution (100 µl; 200 ng per ml) in 8×SSC, 40 mM HEPES (pH 7.4) and 4 mM EDTA was added to the lysate and incubated at 37° C. for 30 minutes. The probe selected here was DNA in nature and specifically hybridising with the ribosomal RNA (rRNA) of *L. monocytogenes*. The hybridization reaction mixture (200 µl) was transferred to a microtiter plate well which had been previously coated with monoclonal anti-probe-target antibodies and incubated at 37° C. for 30 minutes. The plates were then washed 3 times with PBS.

The amplification probe solution (200 µl; 200 ng/µl) in 4×SSC, 20 mM HEPES (pH 7.4) and 2 mM EDTA was added to the wells and incubated at 37° C. for 30 minutes. The plates were then washed 3 times with 0.5M sodium chloride solution. The labelling probe solution (200 µl; 200 ng/µl) in 4×SSC, 20 mM HEPES (pH 7.4) and 2 mM EDTA was added to the wells and incubated at 37° C. for 30 minutes. The plates were washed 3 times with 0.5M sodium chloride solution. Alkaline phosphatase substrate solution (4 mg of p-NPP in 10% diethanolamine and 0.5 mM magnesium chloride, pH 9.8) was added to the wells and incubated at room temperature for 15 to 30 minutes and the color developed was measured at 410 nm in a standard microtiter plate reader.

With the help of positive and negative controls, a colorimetric value was chosen that was statistically distinct between samples that contain and those that do not contain *L. monocytogenes* Using this "cut-off value" the color generated was interpreted as to whether the original sample was positive or negative for the presence of the pathogen.

Below are results of assays performed that detect the presence of *L. monocytogenes*. Assay #1 was performed with biotinylated probe which is 784-bp long; the hybridized probe was detected with a streptavidin-alkaline phosphatase conjugate system. Assay #2 was performed according to the protocol given herein.

| Sample | Status | LPM count (L.m./ml enriched broth) | O.D. 410 Assay #1 | Assay #2 |
|---|---|---|---|---|
| 1 | Positive Control | $3.0 \times 10^4$ | 1.51 | 2.36 |
| 2 | Positive Control | $4.5 \times 10^6$ | 1.63 | 2.6 |
| 3 | Positive Control | $6.0 \times 10^2$ | 1.03 | 1.91 |
| 4 | Positive Control | $5.0 \times 10^6$ | 1.74 | 2.77 |
| 5 | Positive Control | $4.0 \times 10^3$ | 1.23 | 1.98 |
| 6 | Positive Control | $7.0 \times 10^6$ | 1.75 | 2.93 |
| 7 | Negative Control | 0 | 0.08 | 0.06 |
| 8 | Negative Control | 0 | 0.04 | 0.08 |
| 9 | Negative Control | 0 | 0.08 | 0.0 |
| 10 | Negative Control | <10 | 0.05 | 0.16 |
| 11 | Negative Control | 0 | 0.02 | 0.17 |
| 12 | Negative Control | <10 | 0.18 | 0.20 |
| 13 | Unknown | $5.0 \times 10^6$ | 1.60 | 2.56 |
| 14 | Unknown | $6.0 \times 10^4$ | 1.56 | 2.32 |
| 15 | Unknown | $4.0 \times 10^6$ | 1.67 | 2.70 |
| 16 | Unknown | $4.6 \times 10^6$ | 1.70 | 2.74 |
| 17 | Unknown | $7.0 \times 10^5$ | 1.73 | 2.15 |
| 18 | Unknown | $6.0 \times 10^3$ | 1.20 | 1.63 |
| 19 | Unknown | $6.0 \times 10^6$ | 1.77 | 2.45 |
| 20 | Unknown | <20 | 0.08 | 0.16 |

EXAMPLE 3

Assay for the detection of *E. coli* 0157:H7 in meat.

Twenty five grams of the test meat was homogenized for 2 minutes in a stomacher with 250 ml of 1% sterile peptone water and allowed to settle for about 15 minutes. One half ml of the clear upper portion of this homogenate was inoculated into 10 ml of Gram-negative broth (Difco) and incubated at 37° C. for 16–20 hours. Any bacteria in 100 μl of the enriched broth were lysed by mixing the broth with an equal volume of 2% Triton X-100 in a microfuge tube and boiling for 5 minutes at 100° C. The solution was quickly chilled in ice.

Probe solution (100 μl; 200 ng per ml) in 8×SSC, 40 mM HEPES (pH 7.4) and 4 mM EDTA was added to the lysate and incubated at 37° C. for 30 minutes. The probe selected here was RNA in nature and specifically hybridising with the SLT-1 toxin gene of *E. coli* 0157:H7.

The above hybridization reaction mixture (200 μl) was transferred to microtiter plate well which had been previously coated with monoclonal anti-probe-target antibodies and incubated at 37° C. for 30 minutes. The plates were then washed 3 times with PBS.

The amplification probe solution (200 μl; 200 ng/μl) in 4×SSC, 20 mM HEPES (pH 7.4) and 2 mM EDTA was added to the wells and incubated at 37° C. for 30 minutes. The plates were then washed 3 times with 0.5M sodium chloride solution. The labelling probe solution (200 μl; 200 ng/μl) in 4×SSC, 20 mM HEPES (pH 7.4) and 2 mM EDTA was added to the wells and incubated at 37° C. for 30 minutes. The plates were washed 3 times with 0.5M sodium chloride solution.

Alkaline phosphatase substrate solution (4 mg of p-NPP in 10% diethanolamine and 0.5 mM magnesium chloride, pH 9.8) was added to the wells and incubated at room temperature for 15 to 30 minutes and the color developed was measured at 410 nm in a standard microtiter plate reader.

With the help of positive and negative controls, a colorimetric value was chosen that was statistically distinct between samples that contained and those that did not contain *E. coli* 0157:H7. Using this "cut-off value", the color generated was interpreted as to whether the original sample was positive or negative for the presence of the pathogen.

Below are results of assays performed that detect the presence of *E. coli*. The assay was performed with known amounts of *E. coli* inoculated in 25 g of meat which was previously sterilized by gamma irradiation. The assay was performed as described in the protocol given herein.

| Sample | Status | Plate Count | O.D. 410 |
|---|---|---|---|
| 1 | Positive Control | 470 | 1.03 |
| 2 | Positive Control | $3 \times 10^6$ | 2.81 |
| 3 | Positive Control | 532 | 0.99 |
| 4 | Positive Control | $7 \times 10^6$ | 2.73 |
| 5 | Positive Control | $5 \times 10^7$ | 2.8 |
| 6 | Positive Control | $4 \times 10^4$ | 1.98 |
| 7 | Negative Control | 0 | 0.15 |
| 8 | Negative Control | <10 | 0.33 |
| 9 | Negative Control | 0 | 0.0 |
| 10 | Negative Control | 40 | 0.61 |
| 11 | Negative Control | 0 | 0.0 |
| 12 | Negative Control | 0 | 0.04 |
| 13 | Unknown | 56 | 0.59 |
| 14 | Unknown | $6 \times 10^5$ | 2.78 |
| 15 | Unknown | $6 \times 10^4$ | 2.24 |
| 16 | Unknown | 234 | 1.02 |
| 17 | Unknown | $7 \times 10^6$ | 2.75 |
| 18 | Unknown | $7 \times 10^7$ | 2.82 |
| 19 | Unknown | $5 \times 10^6$ | 2.82 |
| 20 | Unknown | $4 \times 10^6$ | 2.79 |

It is to be understood that the examples described above are not meant to limit the scope of the present invention. It is expected that numerous variants will be obvious to the person skilled in the art to which the present invention pertains, without any departure from the spirit of the present invention. The appended claims, properly construed, form the only limitation upon the scope of the present invention.

We claim:

1. A method for enhancing detectable labeling of probe-target complexes in nucleic acid hybridization assays comprising hybridizing a complex of a selected nucleic acid target and a selected primary probe with an amplification probe adapted to permit enhanced detectable labelling of said selected nucleic acid target, said probe comprising at least two regions of nucleic acid sequences: a first region including a sequence complementary to a sequence on said selected primary probe which also contains a sequence complemental to a sequence of said selected nucleic acid target, and a second region including a plurality of discretely labelable mixed polynucleotide sequence units linearly arranged.

2. A method as claimed in claim 1 wherein each said discretely labelable sequence unit comprises a sequence of nucleotide bases hybridizable to a complementary sequence on a labelling probe, said labelling probe covalently attached to a detectable chemical label.

3. A method as claimed in claim 2 wherein the detectable chemical label is selected from an enzymatically active group, a fluorescer, a chromophore, a luminescer, a specifically bindable ligand, or a radioisotope.

4. A method as claimed in claim 1 wherein a label attached to each said discretely labelable sequence units interacts with a reagent member of a label detection system to provide the detectable response.

5. The method as claimed in claim 4 wherein the detectable chemical label is a substrate, cofactor, or inhibitor of an enzyme which is the member of the label detection system with which the label interacts to provide the detectable response.

6. The method as claimed in claim 5 wherein the label is a substrate which is acted on by the enzyme to produce a colorimetric, fluorescent or luminescent signal.

7. The method as claimed in claim 5 wherein the label is a prosthetic group of an enzyme and wherein the apoenzyme of such enzyme is the member of the label detection system with which the label interacts to produce the catalytically active holoenzyme.

8. The method as claimed in claim 7 wherein the prosthetic group is flavin adenine dinucleotide and the apoenzyme is apo(glucose oxidase).

9. A method for detecting specific nucleic acid sequences comprising:

(a) hybridizing a first sequence of a primary polynucleotide probe to a selectable target nucleic acid sequence wherein the primary probe has a means for binding to an amplification probe comprising a nucleic acid sequence adapted to permit enhanced detectable labelling, the amplification probe being capable of hybridizing to at least one labelling probe comprising a nucleic acid sequence conjugated to a chemical label;

(b) immobilizing the target-probe complex;

(c) exposing the immobilized target-probe complex to said amplification probe, such probe comprising at least two regions of nucleic acid sequences: a first region including a sequence complementary to a sequence on a selected primary probe which also contains a sequence complementary to a sequence of said selected nucleic acid target, and a second region including a plurality of discretely labelable mixed polynucleotide sequence units linearly arranged, under conditions that allow the amplification probe to hybridize to the target-probe complex;

(d) exposing the hybridized amplification probe to a labelling probe covalently attached to a detectable chemical label, such probe comprising sequences complementary to sequences on the amplification probe, under conditions that allow many labelling probes to hybridize to the amplification probe;

(e) observing the presence or absence of the detectable chemical label, covalently attached to said labelling probe, in association with the sample as indicating the presence or absence of the target sequence.

10. A method as claimed in claim 9 wherein the means for immobilizing the probe-target complex involves an antibody reagent capable of binding to DNA/DNA, DNA/RNA or RNA/RNA duplexes formed between the selectable target sequence and the complementary primary probe sequence.

11. A method as claimed in claim 10 wherein the antibody reagent is:

(i) selective for binding DNA/RNA hybrids wherein one of the probe and the sequence to be detected is DNA and the other is RNA;

(ii) selective for binding RNA/RNA hybrids wherein both the probe and the sequence to be detected are RNA; or (iii) selective for binding intercalation complexes wherein the duplexes formed in the assay comprise a nucleic acid intercalator bound thereto in the form of intercalation complexes.

12. A method as claimed in claim 9 wherein the detectable chemical label is selected from a enzymatically active group, a fluorescer, a chromophere, a luminescer, a specifically bindable ligand, or a radioisotope.

13. A method as claimed in claim 9 wherein a label attached to each said discretely labelable sequence units interacts with a reagent member of a label detection system to provide the detectable response.

14. The method as claimed in claim 13 wherein the label is a substrate, cofactor, or inhibitor of an enzyme which is the member of the label detection system with which the label interacts to provide the detectable response.

15. The method as claimed in claim 14 wherein the label is a substrate which is acted on by the enzyme to produce a colorimetric, fluorescent or luminescent signal.

16. The method as claimed in claim 14 wherein the label is a prosthetic group of an enzyme and wherein the apoenzyme of such an enzyme is the member of the label detection system with which the label interacts to produce the catalytically active holoenzyme.

17. The method as claimed in claim 16 wherein the prosthetic group is flavin adenine dinucleotide and the apoenzyme is apo(glucose oxidase).

18. The method as claimed in claim 9 applied to the detection of a particular nucleic acid sequence in a test medium wherein the test medium comprises a biological sample which has been subjected to conditions to release and denature nucleic acids present therein.

19. A method as claimed in claim 18 wherein the biological sample includes food substances and the target nucleic acid sequence is of a bacterial microorganism.

20. A method as claimed in claim 18 wherein the biological sample includes food substances and the target nucleic acid sequence is of a virus.

* * * * *